(12) United States Patent
Luthra et al.

(10) Patent No.: US 6,955,682 B2
(45) Date of Patent: Oct. 18, 2005

(54) WOUND CLOSURE SYSTEM AND METHODS

(75) Inventors: Ajay K. Luthra, Ruislip (GB); Shivpal S. Sandhu, Slough (GB); Simon Jon Onis, Brentwood (GB)

(73) Assignee: BioInteractions, Ltd., Berkshire (GB)

( * ) Notice: Subject to any disclaimer, the term of this patent is extended or adjusted under 35 U.S.C. 154(b) by 473 days.

(21) Appl. No.: 10/143,495

(22) Filed: May 9, 2002

(65) Prior Publication Data

US 2003/0018357 A1 Jan. 23, 2003

Related U.S. Application Data

(60) Provisional application No. 60/289,754, filed on May 9, 2001.

(51) Int. Cl.[7] ............................................. A61B 17/08
(52) U.S. Cl. ...................... 606/213; 606/214; 604/4.01
(58) Field of Search ................................ 606/214, 215; 604/4.01, 5.01, 6.07, 6.15, 6.16, 83

(56) References Cited

U.S. PATENT DOCUMENTS

| | | | |
|---|---|---|---|
| 3,916,892 A | * 11/1975 | Letham, Jr. ................... | 604/83 |
| 3,965,896 A | * 6/1976 | Swank ....................... | 604/6.07 |
| 4,373,023 A | 2/1983 | Langer et al. ................ | 435/2 |
| 4,925,665 A | 5/1990 | Murphy ....................... | 424/532 |
| 5,151,192 A | 9/1992 | Matkovich et al. .......... | 210/646 |
| 5,494,590 A | 2/1996 | Smith et al. ................. | 210/782 |
| 5,502,042 A | 3/1996 | Gruskin et al. ............... | 514/59 |
| 5,651,966 A | 7/1997 | Read et al. ............... | 424/93.72 |
| 5,667,963 A | 9/1997 | Smith et al. .................. | 435/2 |
| 5,783,093 A | 7/1998 | Holme ....................... | 210/767 |
| 5,795,571 A | 8/1998 | Cederholm-Williams et al. ....................... | 424/94.64 |
| 5,844,087 A | 12/1998 | Zimmerman et al. ....... | 530/381 |
| 5,897,860 A | 4/1999 | Kim et al. ................. | 424/94.2 |
| 5,906,915 A | 5/1999 | Payrat et al. .................. | 435/2 |
| 5,985,315 A | 11/1999 | Patat et al. ................. | 424/443 |
| 6,054,122 A | 4/2000 | MacPhee et al. .......... | 424/94.4 |
| 6,060,461 A | 5/2000 | Drake ......................... | 514/54 |
| 6,113,948 A | 9/2000 | Heath et al. ................. | 424/499 |
| 6,159,232 A | 12/2000 | Nowakowski .............. | 606/213 |
| 6,197,347 B1 | 3/2001 | Jan et al. .................... | 424/495 |
| 6,238,578 B1 | 5/2001 | Fiehler ....................... | 210/787 |
| 6,245,548 B1 | 6/2001 | Ralston et al. .............. | 435/214 |
| 6,261,258 B1 | 7/2001 | Saines ......................... | 604/58 |
| 6,277,556 B1 | 8/2001 | Grode et al. ................... | 435/2 |
| 6,551,267 B1 | * 4/2003 | Cohen et al. .............. | 604/6.15 |

* cited by examiner

*Primary Examiner*—Julian W. Woo
(74) *Attorney, Agent, or Firm*—Patterson, Thuente, Skaar & Christensen, P.A.

(57) ABSTRACT

A wound closure system and methods utilizes a patient's own blood. The system preferably includes a chamber with a needle and a plunger for transferring and storing blood prior to surgery and the use of reversible anticoagulants. The chamber is pre-loaded with a reversible anticoagulant to prevent the blood from clotting during storage. When the surgery is complete, a counteracting agent is mixed with the withdrawn blood to counteract the reversible anticoagulant and allow the blood to clot. The clottable blood is then reintroduced into the patient to close a wound.

72 Claims, 7 Drawing Sheets

Fig. 2a
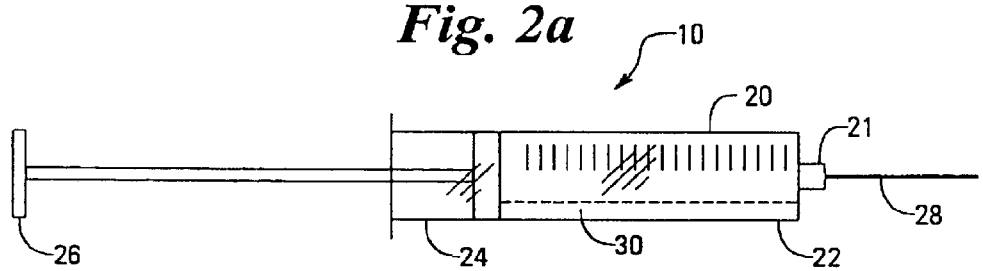
Fig. 2b
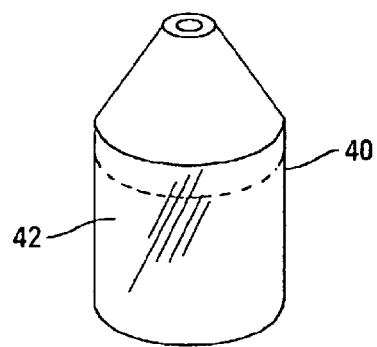
Fig. 2c
Fig. 2d
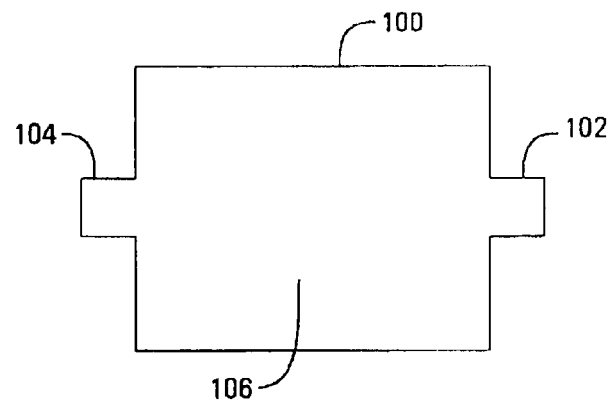

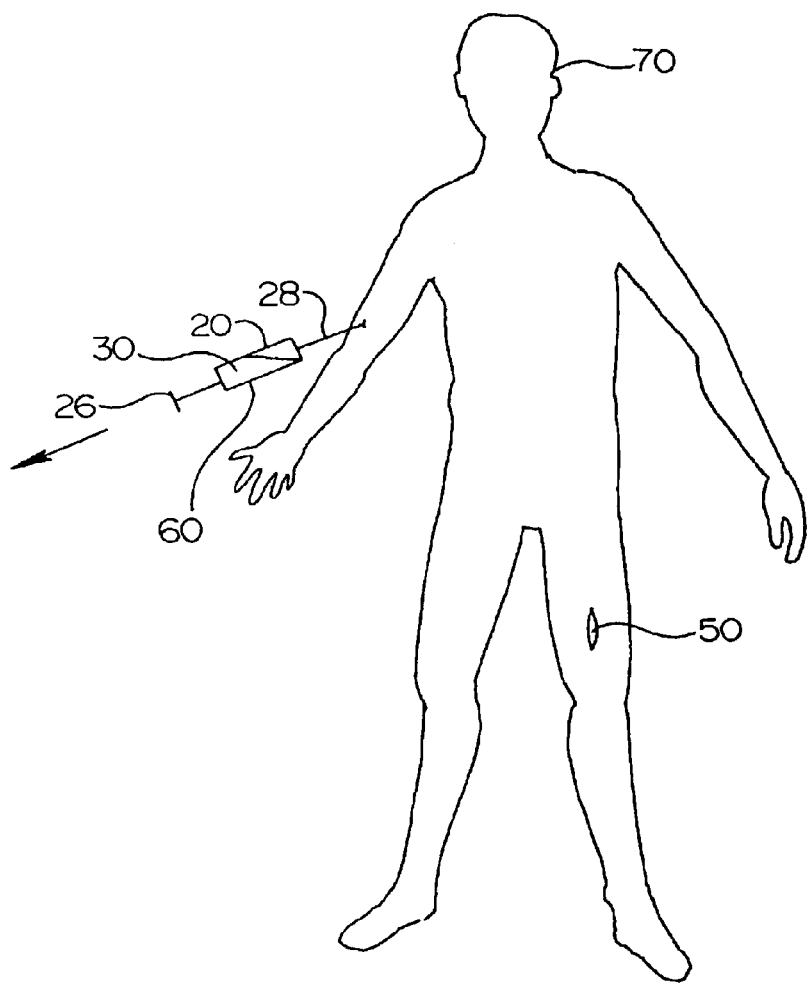

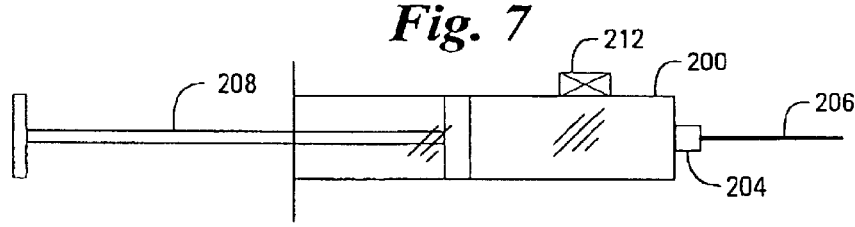
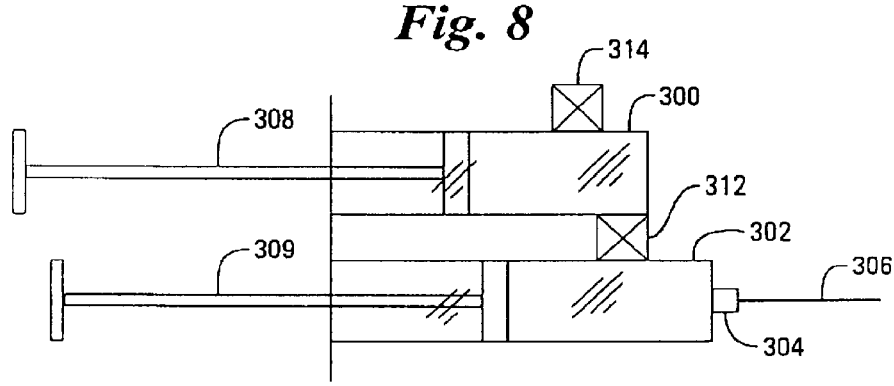
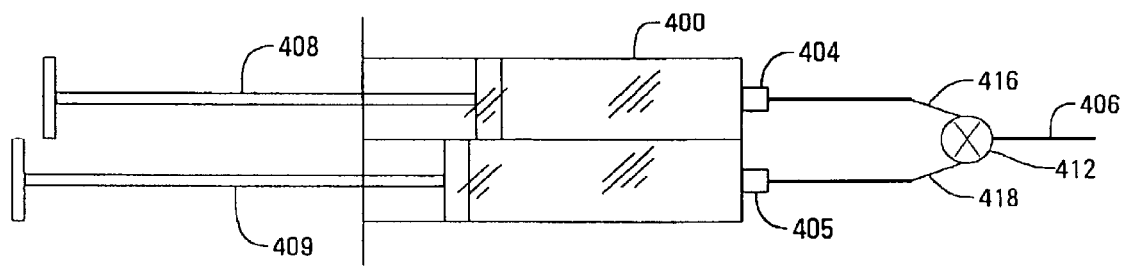

WOUND CLOSURE SYSTEM AND METHODS

RELATED APPLICATIONS

This application claims priority to U.S. Provisional applicaton Ser. No. 60/289,754, filed May 9, 2001, entitled "Wound Closure System and Methods", which is hereby incorporated herein by reference.

FIELD OF THE INVENTION

The invention relates to wound closure systems that use a patient's own blood. More specifically, the invention relates to withdrawing blood from a patient and readministering the blood as a wound closure system.

BACKGROUND OF THE INVENTION

Patients are often treated systemically with anticoagulants that prevent their blood from clotting. Anticoagulants are typically used during medical procedures that require introducing a medical instrument into a patient's body through an artery. An example of such a procedure is a percutaneous transluminal coronary angioplasty (PTCA), which involves introducing a stent through the arteries. Such procedure leave a puncture wound in the artery where the medical instruments, such as a PTCA catheter, are introduced. The puncture extends through the skin, through the tissue under the skin, and into the artery.

Arterial punctures do not close readily, especially when a patient has been treated with an anticoagulant such as heparin. A conventional solution to sealing arterial punctures is to apply pressure to the wound site for many hours after the medical procedure. Another technique is to introduce a small deflated balloon into the artery, inflate it, and pull it up against the puncture so as to seal the artery off from the puncture. Then a coagulant or other clotting agent may be introduced into the puncture without entering the artery. See, for example, U.S. Pat. Nos. 5,108,421; 5,383,986; 5,626,601; and 6,017,359. Once the puncture has sufficiently sealed, the balloon is deflated and removed. Another method involves introducing a temporary or permanent barrier such as a plug, sponge, or gelation slurry. See, for example, U.S. Pat. Nos. 4,890,612; 4,852,568; 5,437,631; 5,782,860; 6,045,570; 6,071,301; and 6,315,753.

Another method includes injecting a wound site or pseudoaneurysm with a coagulant such as thrombin to accelerate clotting at the treatment site. Yet another solution to treating arterial punctures involves treatment of blood in a patient that has been given an anticoagulant such as heparin. In such a procedure, anticoagulated blood is removed from the patient. The blood is then treated to remove the heparin from the blood and then the blood is reintroduced into the patient, see, for example, U.S. Pat. No. 6,159,232 and PCT Application No. PCT/US00/15068, Such treatments conventionally require the use of complicated devices, bioactive coagulants, extra steps for removal of the anticoagulant, or a long delay before the patient can be released.

What is needed is a simple system that reproducibly, safely, and inexpensively provides a quick and effective seal to the wound site of a patient treated with anticoagulants. The use of products derived from blood not taken from the patient or recombinantly produced molecules should preferably be avoided for reasons of safety, cost, and simplicity.

SUMMARY OF PREFERRED EMBODIMENTS OF THE INVENTION

The invention provides a solution for the above-described problems. Before a patient's blood is treated with an anticoagulant, a quantity of blood is taken from the patient. This blood is treated with a reversible anticoagulant so that it is unclottable under normal circumstances. When the blood is required to seal a wound, it is treated so that it will clot when administered to the patient. FIG. 1 depicts a flow chart of preferred embodiments of the invention. Anticoagulated blood is optionally preactivated, then treated with a counteracting agent, optionally undergoes further activation, and is administered to the patient. Storage steps may be included between the treatments.

Preferred embodiments of the invention include a system for closing a wound in a patient that involves a chamber that holds a volume of blood from the patient; a reversible anticoagulant associated with the chamber, an apparatus for transferring the blood between the chamber and the patient; and a counteracting agent for counteracting the reversible anticoagulant. Embodiments of the invention include closing a wound in a patient by withdrawing non-anticoagulated blood from the patient, inhibiting clotting with an anticoagulant; optionally preactivating the blood; storing the blood; reversing the blood by counteracting the activity of the anticoagulant; optionally activating the blood; and applying the blood to the wound.

Another preferred embodiment is a system for closing a puncture wound in a patient. The system includes chamber associated with an anticoagulant; an activating material that a user causes to selectively interact with at least a portion of a volume of blood taken from the patient before the patient is treated with an anticoagulant; and a device to transfer blood from the patient to the chamber after the user causes the activating agent to selectively interact with the portion of the volume of blood. The blood is activated to clot at the wound area of the patient.

BRIEF DESCRIPTION OF THE DRAWINGS

FIG. 2a an embodiment of the invention having a chamber that may be used to transfer blood to and from a patient.

FIG. 2b depicts an embodiment of the invention having a vial that may be used in combination with the chamber of FIG. 2a.

FIG. 2c depicts an embodiment of the invention having a vial that may be used in combination with the chamber of FIG. 2a.

FIG. 2d depicts an embodiment of the invention having a chamber that may be used in combination with the chamber of FIG. 2a.

FIG. 3 depicts the use of the embodiment of the invention depicted in FIG. 2.

FIG. 7 depicts an embodiment of the invention that includes a valve for introducing materials into a chamber.

FIG. 8 depicts an embodiment of the invention that includes a valve for mixing materials in a multi-chambered apparatus.

FIG. 9 depicts an embodiment of the invention having a valve for mixing the contents of a multi-chambered device.

DETAILED DESCRIPTION OF PREFERRED EMBODIMENTS OF THE INVENTION

Figure 1:
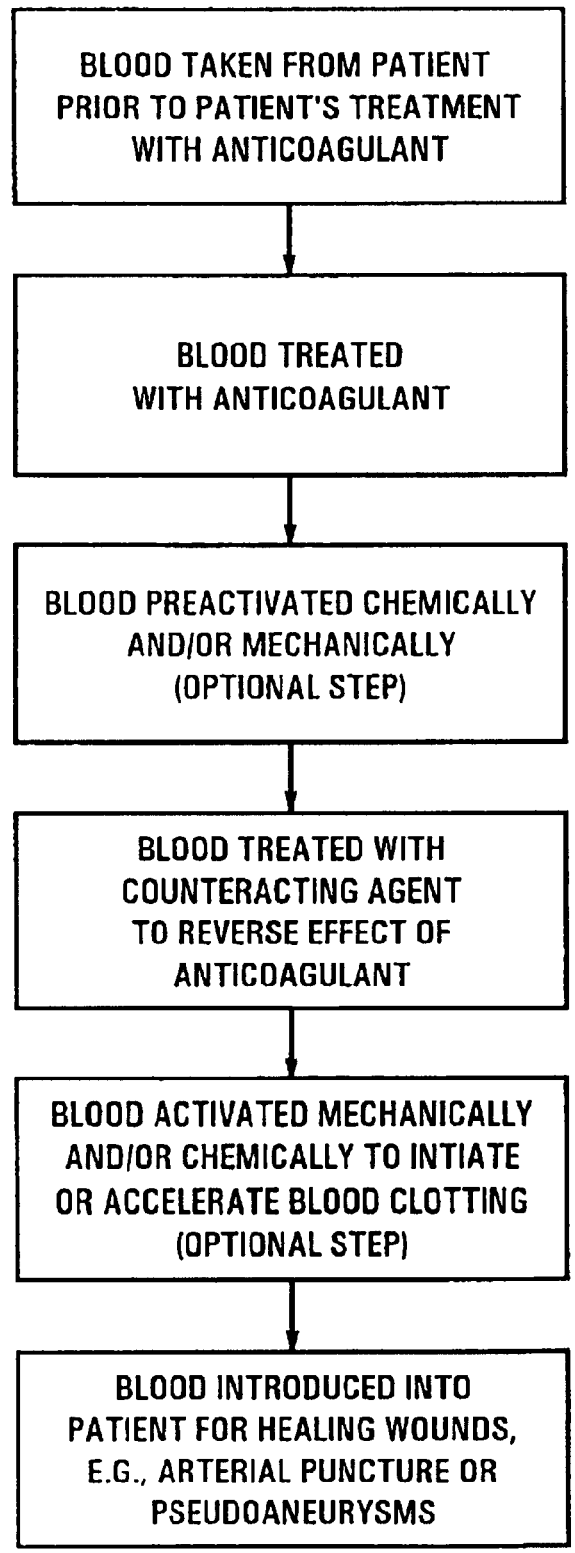
FIG. 1 depicts a flowchart of preferred embodiments of the invention.
Figure 4:
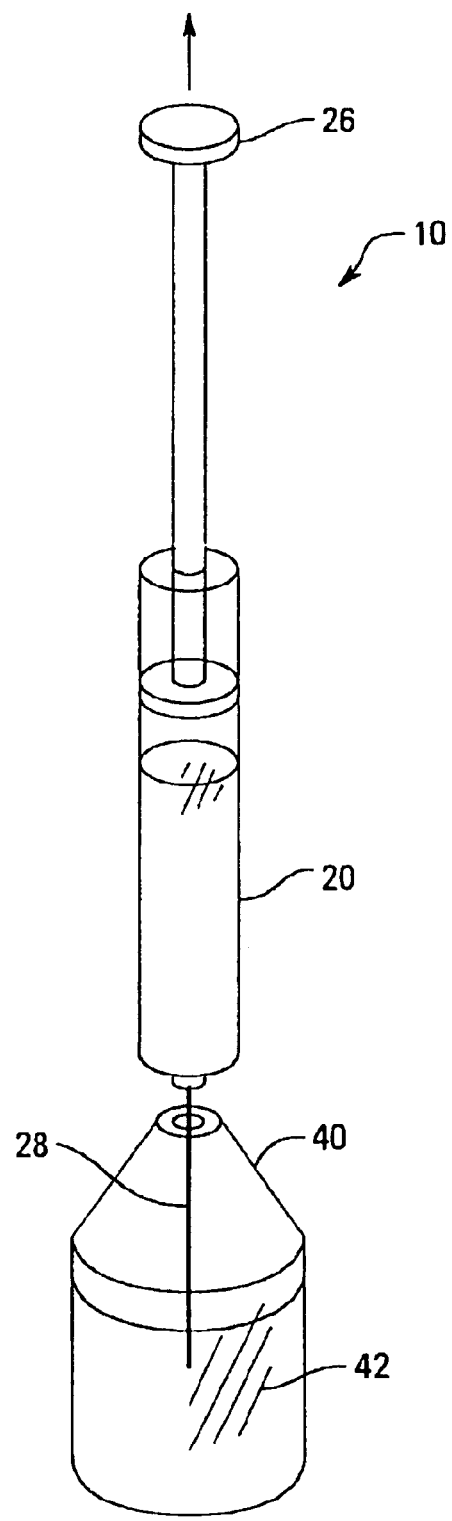
FIG. 4 depicts the chamber of FIG. 1a being used with the vial of FIG. 2b.
Figure 5:
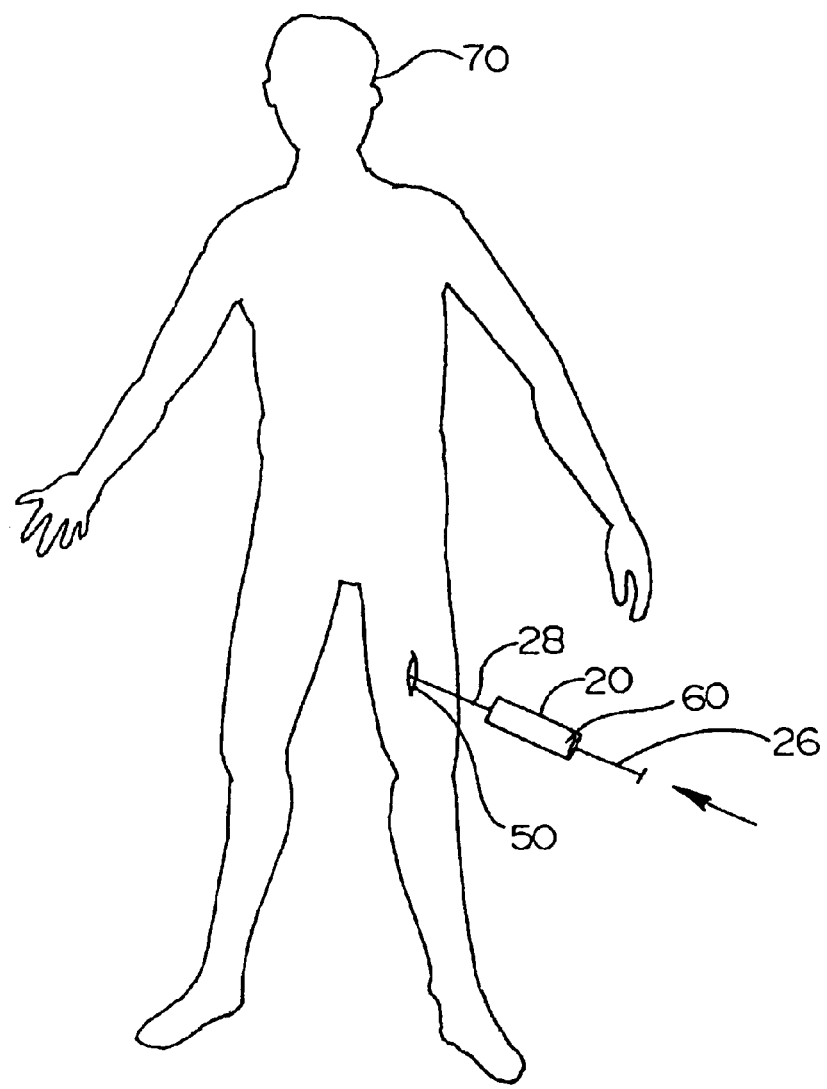
FIG. 5 depicts the chamber of FIG. 2a being used to administer treated blood into the wound of the patient.

Many aspects of the invention relate to the clotting mechanism of blood. Blood circulates with many blood clotting factors present in an unactivated state. An injury normally causes these factors to become activated and to interact with each other to produce a blood clot. The interaction of the activated blood factors occurs in a cascade of events that lead to blood clot formation. There are at least twelve procoagulating clotting factors that can be involved in the blood clotting cascade. Blood that has been stimulated to make these factors active is referred to as activated blood. Stimulation and activation can occur by chemical and mechanical means.

The clotting mechanism can be inhibited by blocking the activity of the clotting factor called thrombin. Thrombin activity is blocked by the binding of antithrombin III to thrombin. Heparin accelerates the inhibition effect exerted by antithrombin on thrombin. Heparin is a commonly used anticoagulant that is added to blood to suppress blood clotting. Blood that is treated with an anticoagulant is referred to as anticoagulated blood.

Some embodiments of the invention involve adding a counteracting agent to anticoagulated blood. The counteracting agent reverses the effect of the anticoagulant so that the blood can clot. Blood that has been anticoagulated and treated with a counteracting agent is termed reversed blood.

Other embodiments of the invention involve activating anticoagulated blood. Some factor(s) of the blood are activated but the blood does not clot because it continues to be anticoagulated. This blood is referred to as preactivated antocoagulated blood. Preactivation causes the blood to be ready to clot so that the clotting mechanism begins to form a clot as soon as the blood is reversed. Table 1 shows some of the combinations of anticoagulations, preactivation, reversal, and activation that are possible. Blood that has been anticoagulated, reversed, activated, or preactivated after its removal from the patient and treatment according to the methods and systems of this invention is referred to as treated blood.

TABLE 1

Treatment of anticoagulated blood

| Preactivation | Reversal of Anticoagulation | Post Activation | Combination |
|---|---|---|---|
| NO | NO | NO | Anticoagulated blood |
| YES | NO | NO | Preactivated anticoagulated blood |
| NO | YES | NO | Reversed blood |
| NO | YES | YES | Reversed activated blood |
| YES | YES | NO | Reversed preactivated blood |
| YES | YES | YES | Preactivated reversed activated blood | disposed in proximal portion 24 of chamber 20 and functions to transfer blood 60 to and from patient 70. Needle 28 is fluidly connected to distal portion 22 of chamber 20 via connector 21. Reversible anticoagulant 30 is in chamber 20. Vial 40 contains counteracting agent 43 for counteracting anticoagulant 30. Vial 40 contains material 42 for chemically or mechanically activating blood. Chamber 100 has connectors 104, 102 for connecting the chamber 20 and needle 28, respectively, and contains material 106 for chemically or mechanically activating blood. As described below, chamber 10, vial 40, 41, and chamber 100 may be used in any variety of combinations.

Referring to FIGS. 2–5, the embodiment of FIG. 2 is shown in use for closing wound 50. Blood 60 is withdrawn from patient 70 before patient 70 is given systemic anticoagulants. Anticoagulant 30 is introduced into chamber 20 and blood 60 is drawn into chamber 20 by introducing needle 28 into patient 70 and pulling plunger 26 away from distal portion 22 of chamber 20. Blood 60 is gently agitated to mix reversible anticoagulant 30 with blood 60. The treated blood is thus anticoagulated and may be stored until needed for further uses.

The anticoagulated blood is introduced into vial 40 via needle 28 where it interacts with activating material 42 and withdrawn back into chamber 10. The blood is now preactivated anticoagulated blood and may be used immediately or stored. The treated blood is then mixed with counteracting agent 43 in vial 41, whereby it becomes more readily clottable. The blood is now reversed preactivated blood. The treated blood is then reintroduced into the patient at wound site 50. Alternatively, chamber 100 may be fitted to chamber 20 via connector 104 and to needle 28 via connector 102. The treated blood is then passed through chamber 100, where it interacts with activating material 106 and passes through needle 28 into wound 50.

The preactivation step of using material 43 in vial 41 to preactivate the antocoagulated blood is optional in some embodiments of the invention. The reversal step of mixing counteracting agent 42 with the treated blood is also optional. The processing of anticoagulated blood requires at least one of the following steps: preactivation, reversal of the anticoagulation agent, or activating the blood after anticoagulation.

The system 10 may be provided in a package or kit that contains chambers 20, 100 and vials 40, 41 with reversible anticoagulant 30, and activating materials 42, 106. Such a kit or package may have reversible anticoagulant 30, blood activating material 42, 106 and counteracting agent 43 preweighed, prealiquoted, in solid-phase or in solution. The members of the kit or package may be associated with each other in a container such as a box or other container such as a cardboard backing equipped with plastic "blisters." An embodiment of the invention includes instructions with the kit. Instructions may be written or graphical and, for example, include a plot of blood volume versus reversible anticoagulant 30/counteracting agent 43. System 10 may include devices for mixing the blood with other components of system 10. System 10 may include indicators for indicating when the treated blood is ready to be reintroduced. Chamber 20 may be multi-chambered to accommodate storage of reversible anticoagulant 30, blood activating material or technique 42 and counteracting agent 43 within a common structure. Plunger 26 may be manual or automated and multiple plungers may be used, for example, if counteracting agent is contained in a portion of a multi-chamber arrangement of chamber 20.

Figure 6:
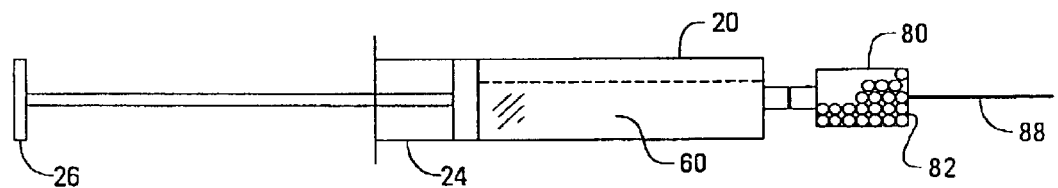
FIG. 6 depicts an alternative embodiment of the invention that includes a chamber for activating blood introduced into a patient's wound.

FIG. 6 depicts an alternative embodiment of the invention. In this embodiment, needle 28 is removed from chamber 20 after counteracting agent 43 is added to chamber 20 and ancillary chamber 80 containing glass beads 82 that act to accelerate and or initiate clotting of blood 60 in attached chamber 20. Ancillary chamber 80 includes application needle 88 for reintroducing blood 60 into patient 70 at wound site 50.

FIG. 7 depicts an embodiment of the invention having chamber 200 with connector 204 attached to needle 206 with plunger 208 partially disposed in chamber 200. Valve 212 allows fluids to be introduced or withdrawn from chamber 200, for example by connecting another syringe or insertion of a needle. In use, blood is drawn into chamber 200 through needle 206 and connector 204 by operation of plunger 208. Chamber 200 is preferably preloaded with anticoagulant (not shown) and preactivating agents (not shown). Counteracting agent (not shown) is introduced into chamber 200 through valve 212 to reverse blood in the chamber prior to the reintroduction of the blood to the patient.

FIG. 8 depicts an embodiment of the invention having compartments 300, 302 with connector 304 attached to needle 306 with plungers 308, 309 partially disposed in compartments 300, 302 respectively. Valve 312 allows fluids to communicate between compartments 300 and 302. Optional valve 314 allows fluids to be introduced or removed from compartment 300, for example by connecting another syringe or insertion of a needle. In use, blood is drawn into compartment 302 through needle 306 and connector 304 by operation of plunger 309. Compartment 302 is preferably preloaded with anticoagulant (not shown) and preactivating agents (not shown). Counteracting agent (not shown) is moved from compartment 300 into compartment 302 through valve 312 to reverse blood in the chamber prior to the reintroduction of the blood to the patient.

FIG. 9 depicts an embodiment of the invention having compartments 400, 402 with connectors 404, 405 attached to conduits 416, 418, respectively, with plungers 408, 409 partially disposed in chambers 400, 402 respectively. Conduits 416, 418 communicate with three-way valve 412. Three-way valve 412 allows fluids to communicate between compartments between any two of conduits 416, 418 and needle 406. In use, blood is drawn into compartment 402 through needle 406, conduit 418, and connector 405 by operation of plunger 409. Compartment 402 is preferably preloaded with anticoagulant (not shown) and preactivating agents (not shown). Counteracting agent (not shown) is moved from compartment 400 into compartment 402 through three-way valve 412 to reverse blood in the chamber prior to the reintroduction of the blood to the patient. Three-way valve 412 is moved so that blood is forced from compartment 402 out through needle 406 by operation of plunger 409.

An embodiment of the invention includes the use of a reversible anticoagulant that binds calcium ions in blood to prevent clotting. Most chemical species that contain anionic groups including sulphates, sulphonates, carboxyl groups, phosphates, oxalates, and citrates are suitable calcium-binding materials. Drugs such as ciproflaxin, quinolones, doxycycline, lymecycline, minocycline, and penicillamine may also used as a reversible anticoagulant to bind calcium ions to prevent clotting. Ion exchange resins may also be used for example, to remove calcium ions to prevent clotting via calcium ion dependent serine proteases. Preferably, the reversible anticoagulant that binds calcium ions is either sodium citrate, citric acid, biscitrate, ethylenediaminetetraacetic acid (EDTA) or ethylene glycol-bis(2-aminoethyl) tetraacetic acid (EGTA). Thus counteracting agents that include materials/compounds that add or replace calcium ions to blood may be used to counteract reversible anticoagulants that bind calcium ions.

Another embodiment includes the use of a reversible anticoagulant that activates and/or potentiates natural inhibitors of the clotting cascade. Examples of these inhibitors include heparin salts (e.g., ammonium, lithium, and sodium salts), their derivatives, and pentasaccharide (e.g., heparan's). Counteracting agents 43 used to counteract heparin salts and their derivatives include protamine, polybrene, and heparinase. Counteracting agents of heparin salts may also include chemical/mechanical removal of the inhibitor, as described, for example, in PCT application WO 00/74575, entitled "Clotting Cascade Initiating Apparatus And Methods Of Use" which is hereby incorporated by reference herein. NEUTRALASE™ may be used as a counteracting agent for pentasaccharide.

Other reversible anticoagulants contemplated in embodiments of the invention include materials that directly bind clotting factors or inhibit activation. Examples of reversible anticoagulants that are clotting factors binders include hirudin and its derivatives. Other reversible anticoagulants include materials or processes that change the ionic balance of the blood, the pH balance of the blood, or cool the blood. The ionic balance can be changed by the addition of salts, e.g., sodium chloride; the pH can be changed by the addition of a base or acid.

One advantage of the invention is that blood may be treated with a known amount of anticoagulant and reverse with a precise amount of counteracting agent that has been calculated to counter the anti-coagulant. Alternatively, an excess or undersupply of anticoagulant or counteracting agent may be used so as to tightly and reproducibly control blood behavior.

A clotting agent, as used herein, means factors that stimulate, activate, or potentiate blood to clot, e.g., collagen and thrombin, and other agents that cause blood to clot, e.g., such as shear forces, glass particles, and many types of polymeric fibers. Examples of polymeric fibers include polyester, polyamide, polypropylene, polyethylene, and others.

Clotting agents work by chemical pathways and mechanical pathways. Chemical pathways include biologic and non-biologic materials and/or factors that activate blood. A clotting agent includes non-biologic materials that cause blood clotting because of their physical origin, e.g., sand, diatomaceous earth, silicates of many types kaolin, (hydrated aluminum silicate), celite, aluminum ions, e.g. styptic stick used to close wound after shaving, titanium, dextran sulfate, and certain ions linked to a solid phase. A clotting agent also includes clotting agents having a biological origin, e.g., skin, cotton wool, fatty acids, ellagic acid, cartilage, collagen, gelatin, sulfatide, thromboplastin, certain membranes, phospholipids and cytokines. Other clotting agents of biologic origin are natural or synthetic components of the clotting cascade, e.g., activating serine proteases, activating platelet factors and proteins and activating cofactors, and clot activating venoms. Contact activation occurs when a member of the blood's clotting cascade is activated by contact with a surface. Contact activation, e.g., via the intrinsic pathway, is considered part of a chemical pathway of activation, as the term is used herein, since it usually acts by activating a member of the contact pathway.

The mechanical pathways of clotting agents include the use of devices or fluid flow forces to elicit blood stimulation or activation. Mechanical pathways include, for example, the creation of shear forces sufficient to activate blood. Blood may be forced through, for example, a bed of beads, through a sponge or matrix, between two plates to create sufficient shear. Alternatively, a device that is introduced into a chamber holding blood may be used to agitate the blood and create shear forces; for example, a fan, a crank, and a multi-armed rotating mechanism. Alternatively, an agitation device, e.g., a vortex mixer, may be used to rapidly move blood to create shear to turbulence. Alternatively, a device, e.g., spheres, may be introduced such a chamber while it is agitated to enhance activation.

Another embodiment of the invention includes using material or techniques that activate blood to cause or accelerate blood clotting in addition to counteracting reversible anticoagulants. Such techniques may be used to initiate and/or accelerate the clotting of blood. Such techniques include, for example, exposing the withdrawn blood to glass (or sintered glass, or glass-equivalent) beads, fibers, matrices, sponges, or filters; introducing thrombin-like enzymes and/or analogues; or using other agents known to those skilled in these arts. Such materials may be solid, non-round, irregularly shaped, porous, and/or permeable to blood.

Certain embodiments of the invention include the use of methods and materials for the preventing the break down of blood clots by lytic agents. Lytic agents are agents the chemically break down blood clots, for example by enzymatic action. Lytic agents include plasmin, plasminogen, plasminogen activators, tissue plasminogen activator, streptokinase, and urokinase plasminogen activator. Antilytic agents are agents that inhibit lytic agents and include aprotinin, epsilon amino caproic acid, antibodies against lytic agents, peptides that bind to lytic agents, peptides or chemicals that bind to the binding sites of lytic agents or the sites of a blood clot that lytic agents bind, and other agents and peptides known to those skilled in these arts. The breakdown of clots can be inhibited in some embodiments of the invention by removing lytic agents. Lytic agents can be removed by exposing the blood to matrices that contain factors that bind the lytic agents.

A pseudoaneurysm sometimes forms when blood seeps from the puncture into the tissue outside of the artery or vein. Blood in the pseudoaneurysm, since it has often undergone systemic anticoagulatin, is slow to clot and dissipate. The pseudoaneurysm may grow with time and cause discomfort and tissue damage. Some embodiments of the invention may be used to treat pseudoaneurysms by drawing blood from the pseudoaneurysm or other portion of the body into chamber 20, preactivating it, treating it to counteract the anticoagulants in the blood, and reintroducing the treated blood into the patient. Steps of removing anticoagulants and activating the blood after it has been reversed may optionally be included. Treatment of a wound under the skin of a patient includes, but is not limited to, treatment of a pseudoaneurysm, arterial puncture, and venous puncture. The term skin, as used herein, means the surface of a patient's epidermis.

Blood, as used herein unless otherwise indicated, is a broad term that includes whole blood, fluids that contain whole blood or fractions of whole blood, blood that has been treated with anticoagulants, and blood that has been reacted to remove anticoagulants or to clot. Anticoagulants means substances administered to a living patient that inhibit or slow the blood clotting time of the patient, including those that work through activating or potentiating natural inhibitors of the clotting cascade, e.g., heparin, heparin derivatives, pentasaccharides; and those that work by directly binding the clotting factors or inhibiting activation, e.g., hirudin and its derivatives, enzyme inhibitors, or conditions that minimize enzyme activity, and calcium binders, e.g., EDTA.

Clotting agents may be used in a chamber that receives the blood or in other chambers or compartments that contact the blood, be immobilized to portions of the device, or entrapped in matrices associated with the device. Clotting agents may be used to accelerate blood clotting so blood cleansed of anticoagulants maybe more readily clotted. Such agents may be present, for example, in the blood receiving chamber. Immobilization is preferably by covalent bonding but adsorption to a surface or entrapment in a matrix may also be used. Covalent immobilization techniques are known to skilled artisans, see, for example, "Bioactive Biomaterials", *Curr Opin Biotechnol* 1999 Apr.; 10(2) :123–9. Another embodiment of the invention includes immobilizing coagulant molecules such as thrombin in the solid phase such that it does not leave the solid phase within vial 40 or chambers 80, 100. For example, thrombin may be immobilized to the solid phase of a non-specifically acting polymer such as polyethyleneimine (PEI) by adsorption, trapped in a matrix, or covalently bound.

The chambers and vials of the system are preferably sterile so that blood may be returned to the patient without infection. Chambers 20, 100 and/or vials 40, 41 may be substituted with other suitable vessels or be part of a multi-chambered device. A blood filter that filters blood to remove infectious agents before it is returned to the patient may also be used. A preferred filter selectively removes infectious agents. The chamber(s) and/or vial(s) are preferably fully enclosed so as to prevent the entry of contaminants after sterilization. Suitable include syringes, chambers in a dual- or multi-barreled syringes, vials, catheters, tubes, pipettes, and mixers. Agents may be introduced in the containers as is suitable, for example, as solutions, fluids, solids, and powders.

Experiments showed that a patient's blood can be withdrawn, treated with a reversible anticoagulant, stored, reversed, and clotted with or without clotting agents (Table 2). Testing was conducted with 15 human volunteers to demonstrate certain aspects of the invention. 15 ml of blood was drawn into a 20 ml syringe containing 1 ml of sodium citrate buffer and, in certain samples, 0.3 g of glass wool. The blood was stored at 37° C. or at room temperature for 1 hour and then transferred to a glass tube or a siliconized polypropylene syringe having the amount of calcium ions calculated to reverse the effect of the sodium citrate. The resultant clotting time was measured at 37° C., with clotting determined to be the point at which inversion of tube or syringe did not dislodge the clot from its bottom and essentially no fluid flowed out of the clot. Thus the blood was anticoagulated by the sodium citrate and reversed upon exposure to the calcium ions. Samples exposed to a glass test tube were indicative of an activation step after reversal because glass is highly contact-activating compared to the siliconized syringes. The glass wool was indicative of pre-activation since glass activates blood and the glass wool was present in the blood while it was anticoagulated.

The fastest mean clotting time was 2.2 minutes (Table 2) when the reversed blood was preactivated by being exposed to glass wool. In contrast, reversed blood that was not preactivated required a mean time of 14.6 minutes to clot in the same container. When no preactivation step glass wool was omitted, the mean clotting time was 15. 9 minutes. When the glass wool was omitted and a glass test tube was substituted for the polypropylene syringe, the mean clotting time was 5.2 minutes. When the blood storage step and the glass wool were both omitted, the mean clotting time in a glass test tube was 5.7 minutes and in a polypropylene syringe was 15.9 minutes. For each set, n=3. Table 2, below, summarizes the results of the testing.

Apparatus and methods for transferring blood 60 between chamber 20 and patient 70 include use of syringes, catheters, introducers, and other techniques known to those skilled in these arts, including techniques for accurately placing the introduced blood in wound 50.

TABLE 2

Clotting times for anticoagulated reversed blood

| Treatment | Blood Condition | Mean Time to Full Clot* (min) | Standard Deviation (min) | Range (min) |
|---|---|---|---|---|
| Pre-Activation PP Siliconized Syringe, 1-hr Storage | Reversed, preactivated | 2.2 | 0.4 | 2.0–3.0 |
| PP Siliconized Syringe No Storage, no glass wool | Reversed | 15.9 | 3.3 | 12.1–20.3 |
| Baseline-PP Siliconized Syringe 1-hr Storage, no glass wool | Reversed | 14.6 | 1.8 | 15.0–15.3 |
| Baseline-Glass Tube No Storage, no glass wool | Reversed, activated | 5.7 | 0.3 | 5.3–6.4 |
| Baseline-Glass Tube 1-hr Storage, no glass wool | Reversed, activated | 5.2 | 0.4 | 4.8–6.0 |

*The clotting times are the same irrespective of the blood being stored at 37° C. or at room temperature.

The embodiments described herein merely illustrate examples of the present invention and actual compositions or materials used may vary somewhat. The invention is not to be unduly limited to the exact materials and methods described herein but is also to include materials and methods known to those skilled in these arts. Patents and patent applications cited in this document are hereby incorporated herein by reference.

What is claimed is:

1. A system for closing a puncture wound in a patient comprising:
   a chamber that accommodates a volume of blood from the patient;
   a preloaded reversible anticoagulant in the chamber;
   a counteracting agent for counteracting the reversible anticoagulant that user causes to selectively interact with at least a portion of the volume of blood; and
   an apparatus to transfer the volume of blood from the patient to the chamber and to transfer the portion of the volume of blood from the chamber to the puncture wound after the user causes the counteracting agent to selectively interact with the portion of the volume of blood.

2. The system of claim 1 further comprising:
   an activating material for activating the portion of the volume of blood after the user causes the counteracting agent to selectively interact with the portion of the volume of blood.

3. The system of claim 2 wherein the activating material is non biological in origin.

4. The system of claim 3 wherein the activating material is chosen from a group consisting of glass, silica sand, dextran sulfate, and celite.

5. The system of claim 3 wherein the activating material is chosen from a group consisting of ions and metals.

6. The system of claim 5 wherein the activating material comprises titanium.

7. The system of claim 3 wherein the activating material is a polymer.

8. The system of claim 7 where the polymer is selected from a group consisting of silicone, polyester, polyurethane, polycarbonate, nylon, polyvinylchloride, polyethylene and polyethyleneimine.

9. The system of claim 2 wherein the activating material is biological in origin.

10. The system of claim 9 wherein the activating material is chosen from a group consisting of cotton, diatomaceous earth, collagen, and gelatin.

11. The system of claim 9 wherein the activating material is chosen from a group consisting of thromboplastin, cephalin, ellagic acid, fatty acid, and sulfatide.

12. The system of claim 9 wherein the activating material is a procoagulating or coagulating clotting cascade member or an analogue thereof.

13. The system of claim 1 wherein the apparatus utilizes a common conduit to transfer the volume of blood to the chamber and to transfer the portion of the volume of blood to the puncture wound.

14. The system of claim 1 wherein the apparatus includes at least one conduit selected from a set consisting of a needle and a catheter.

15. The system of claim 1 wherein the chamber includes multiple compartments, at least one of which accommodates the volume of blood and at least another of which accommodates the counteracting agent and is selectively brought into fluid communication with the at least one compartment accommodating the volume of blood.

16. The system of claim 1 wherein the counteracting agent is contained in a vial separate from the chamber that the user causes to selectively interact with the portion of the volume of blood.

17. The system of claim 1 wherein the reversible anticoagulant is an agent that binds calcium ions in the volume of blood.

18. The system of claim 1 wherein the apparatus for transferring blood between the chamber and the patient is selected from a set consisting of a needle and a catheter.

19. The system of claim 1 wherein the chamber for receiving the blood is multi-chambered.

20. The system of claim 1 wherein the counteracting agent is contained in a vial separate from the chamber.

21. The system of claim wherein the reversible anticoagulant binds calcium ions.

22. The system of claim 1 wherein the reversible anticoagulant competitively inhibits the action of calcium ions and results in inhibition of clotting factors.

23. The system of claim 1 wherein the anticoagulant effect can be reached via a physical change of pH or temperature.

24. The system of claim 23 wherein the physical change is a change of temperature.

25. The system of claim 1 wherein the reversible anticoagulant is selected from a group consisting of sodium citrate, isocitrate, citric acid, EDTA and EGTA.

26. The system of claim 1 wherein the reversible anticoagulant is selected from a group consisting of oxalates, phosphates, phylate, and cation chelators.

27. The system of claim 1 wherein the reversible anticoagulant is selected from a group consisting of heparin, hirudin, pentasaccharide, low molecular weight heparin, low molecular weight heparinoid, and heparan sulfate.

28. The system of claim 1 wherein the counteracting agent is selected from a group consisting of protamine, polybrene, and heparinase.

29. The system of claim further comprising anti-lytic agents selectively exposable to the volume of blood by a user.

30. The system of claim 1 further comprising lytic-binding materials that bind lytic agents in at least a portion of the blood.

31. The system of claim 1 wherein the system is disposed in a kit contained in a sterile package.

32. The system of claim 31 further comprising instructions on use of the kit.

33. A system for treating a wound in a patient comprising:
means for storing blood;
means for transferring blood between means for storing blood and the patient;
means for inhibiting blood clotting preloaded in the means for storing blood; and
means for counteracting the means for inhibiting blood clotting and connected to the means for storing blood.

34. A method for treating a wound in a patient comprising:
withdrawing a volume of blood from the patient into a chamber, the blood being substantially free of anticoagulants;
inhibiting clotting of the volume of blood with an anticoagulant preloaded in a chamber storing the volume of blood in the chamber;
applying a counteracting agent to at least a portion of the volume of blood to counteract the action of the anticoagulant; and
applying the portion of the volume of blood to the wound.

35. The method of claim 34 further comprising applying the volume of blood to the wound by introducing the portion of the volume of the blood to the vicinity of the wound.

36. The method of claim 35 wherein the anticoagulant is selected from a group consisting of calcium ion binders, sodium citrate, isocitrate, citric acid, EDTA, EGTA, oxalates, phosphates, phylate, and cation chelators.

37. The method of claim 35 wherein the anticoagulant is selected from a group consisting of heparin, hirudin, pentasaccharide, low molecular weight heparin, DANAPAROID™, protamine, polybrene, and heparinase.

38. The method of claim 35 further comprising exposing the volume of blood to anti-lytic agents.

39. The method of claim 34 further comprising activating the portion of the volume of blood with an activating material.

40. The method of claim 39 wherein the activating material is non bilogical in origin.

41. The method of claim 40 wherein the activating material includes a material chosen from a group consisting of glass, silica sand, and celite, ions, metals, titanium, lextran sulfate, and polymer.

42. The method of claim 39 wherein the activating material is biological in origin.

43. The method of claim 42 wherein the activating material is chosen from a group consisting of cotton, diatomaceous earth, collagen, and gelatin, thromboplastin, cephalin, ellagic acid, fatty acid, sulfatide, a procoagulating member of the clotting cascade, and procoagulating member of the clotting cascade analogues.

44. The method of claim 34 wherein applying the counteracting agent includes moving the counteracting agent from a first compartment in the chamber to a second compartment in the chamber.

45. The method of claim 34 further comprising transferring blood between the chamber and the patient using a member of the set consisting of a needle and a catheter.

46. A system for treating a wound in a patient comprising:
a chamber that accommodates a volume of blood from the patient;
a preloaded reversible anticoagulant in the chamber;
an activating material that a user causes to selectively interact with at least a portion of the volume of blood; and
an apparatus to transfer the volume of blood from the patient to the chamber and to transfer the portion of the volume of blood from the chamber to the wound after the user causes the activating material to selectively interact with the portion of the volume of blood.

47. The system of claim 46 wherein the activating material is non biological in origin.

48. The system of claim 47 wherein the activating material includes a material chosen from a group consisting of glass, silica sand, celite, ions, metals, titanium, dextran sulfate, and polymer.

49. The system of claim 46 wherein the activating material is biological in origin.

50. The system of claim 49 wherein the activating material is chosen from a group consisting of cotton, diatomaceous earth, collagen, and gelatin, thromboplastin, cephalin, ellagic acid, fatty acid, sulfatide, a procoagulating member of the clotting cascade, and procoagulating member of the clotting cascade analogues.

51. The system of claim 46 wherein the apparatus utilizes a common conduit to transfer the volume of blood to the chamber and to transfer the portion of the volume of blood to the puncture wound.

52. The system of claim 46 wherein the activating material is contained in a vial separate from the chamber.

53. The system of claim 46 wherein the reversible anticoagulant binds calcium ions.

54. The system of claim 46 wherein the reversible anticoagulant is selected from a group consisting of sodium citrate, isocitrate, citric acid, EDTA and EGTA.

55. The system of claim 46 wherein the reversible anticoagulant is selected from a group consisting of oxalates, phosphates, phylate, and cation chelators.

56. The system of claim 46 wherein the reversible antocoagulant is selected from a group consisting of heparin, hirudin, pentasaccharide, low molecular weight heparin, and DANAPAROID™.

57. The system of claim 46 wherein the counteracting agent is selected from a group consisting of protamine, polybrene, and heparinase.

58. The system of claim 46 further comprising anti-lytic agents selectively exposable to the volume of blood by a user.

59. The system of claim 46 further comprising lytic-binding materials that bind lytic agents in at least a portion of the blood.

60. The system of claim 46 wherein the system is disposed in a kit contained in a sterile package.

61. The system of claim 46 further comprising instructions on use of the kit.

62. A method for treating a wound in a patient comprising:
withdrawing an volume of blood from the patient into a chamber, the blood being substantially free of anticoagulants;
inhibiting clotting of the volume of blood with an anticoagulant preloaded in the chamber;
storing the volume of blood in the chamber;
exposing at least a portion of the volume of blood to an activating material; and
applying the portion of the volume of blood to the wound.

63. The method of claim 62 further comprising applying the volume of blood to the wound by introducing the portion of the volume of the blood to the vicinity of the wound.

64. The method of claim 62 wherein the activating material is non biological in origin.

65. The method of claim 64 wherein the activating material includes a material chosen from a group consisting of glass, silica sand, celite, ions, metals, titanium, dextran sulfate, and polymer.

66. The method of claim 62 wherein the activating material is biological in origin.

67. The method of claim 66 wherein the activating material is chosen from a group consisting of cotton, diatomaceous earth, collagen, and gelatin, thromboplastin, cephalin, ellagic acid, fatty acid, sulfatide, a procoagulating member of the clotting cascade, and a procoagulating member of the clotting cascade analogues.

68. The method of claim 62 wherein applying the counteracting agent includes moving the counteracting agent from a first compartment in the chamber to a second compartment in the chamber.

69. The method of claim 62 further comprising transferring blood between the chamber and the patient using a member of the set consisting of a needle and a catheter.

70. The method of claim 62 wherein the anticoagulant is selected from a group consisting of calcium ion binders, sodium citrate, isocitrate, citric acid, EDTA, EGTA, oxalates, phosphates, phylate, and cation chelators.

71. The method of claim 62 wherein the anticoagulant is selected from a group consisting of heparin, hirudin, pentasaccharide, low molecular weight heparin, DANAPAROID™, protamine, polybrene, and heparinase.

72. The method of claim 62 further comprising exposing the volume of blood to anti-lytic agents.

* * * * *

(12) EX PARTE REEXAMINATION CERTIFICATE (7754th)
United States Patent
Luthra et al.

(10) Number: US 6,955,682 C1
(45) Certificate Issued: Sep. 21, 2010

(54) WOUND CLOSURE SYSTEM AND METHODS

(75) Inventors: Ajay K. Luthra, Ruislip (GB); Shivpal S. Sandhu, Slough (GB); Simon Jon Onis, Brentwood (GB)

(73) Assignee: Escanaba Holdings, Inc., Tortola (VG)

Reexamination Request:
No. 90/009,473, May 29, 2009

Reexamination Certificate for:
Patent No.: 6,955,682
Issued: Oct. 18, 2005
Appl. No.: 10/143,495
Filed: May 9, 2002

Related U.S. Application Data

(60) Provisional application No. 60/289,754, filed on May 9, 2001.

(51) Int. Cl.
*A61B 17/08* (2006.01)

(52) U.S. Cl. .......... 606/213; 606/214; 604/4.01
(58) Field of Classification Search .......... None
See application file for complete search history.

(56) References Cited

U.S. PATENT DOCUMENTS

| | | | |
|---|---|---|---|
| 3,223,083 A | 12/1965 | Cobey | |
| 4,277,463 A | 7/1981 | Tomic | |
| 4,347,243 A | 8/1982 | Schneider | |
| 4,359,049 A | 11/1982 | Redl et al. | |
| 4,852,568 A | 8/1989 | Kensey | |
| 5,000,854 A | 3/1991 | Yang | |
| 5,192,300 A | 3/1993 | Fowler | |
| 5,275,616 A | 1/1994 | Fowler | |
| 5,292,332 A | 3/1994 | Lee | |
| 5,310,407 A | 5/1994 | Casale | |
| 5,318,524 A | 6/1994 | Morse et al. | |
| 5,383,896 A | 1/1995 | Gershony et al. | |
| 5,413,571 A | 5/1995 | Katsaros et al. | |
| 5,413,786 A * | 5/1995 | Anraku .......... | 514/185 |
| 5,437,292 A | 8/1995 | Kipshidze et al. | |
| 5,443,481 A | 8/1995 | Lee | |
| 5,447,502 A | 9/1995 | Haaga | |
| 5,510,102 A * | 4/1996 | Cochrum .......... | 424/78.08 |

(Continued)

FOREIGN PATENT DOCUMENTS

| | | |
|---|---|---|
| EP | 0 466 178 B1 | 7/1991 |
| JP | 06-181979 | 7/1994 |

OTHER PUBLICATIONS

Valeri et al, "Effects of temperature of bleeding time and clotting time in normal male and female volunteers", Crit. Care Med., 1195 April, 23(4):698–704.*
Crowell et al, "Effect of acidity on blood coagulation", Am. J. Physiol., Aug. 1961, 200:379–82*
Markus et al, "Quantitative determination of the binding of epsilon–aminocaproic acid to native plasminogen", J. Biol. Chem. Feb. 10, 1978, 253(3):727–32.*
Mahdishassan Ph.D., "Blood as the Earliest Drug, Its substitutes, Preparations and Latest Position", American Journal of Chinese Medicine, XIV(3–4):104–109 (1986).
Orlikowski et al., "Effect of Delay and Storage on Whole–Blood Clotting Analysis as Determined by Thrombelastography", J. Clinical Monitoring, 9:5–8 (1993).
Varshney et al., "Effect of Various Biostimulators on Clinical Wound Healing in Bovines", Indian Vet. J., 65:436–439 (May 1988).

*Primary Examiner*—Cary E. Wehner

(57) ABSTRACT

A wound closure system and methods utilizes a patient's own blood. The system preferably includes a chamber with a needle and a plunger for transferring and storing blood prior to surgery and the use of reversible anticoagulants. The chamber is pre-loaded with a reversible anticoagulant to prevent the blood from clotting during storage. When the surgery is complete, a counteracting agent is mixed with the withdrawn blood to counteract the reversible anticoagulant and allow the blood to clot. The clottable blood is then reintroduced into the patient to close a wound.

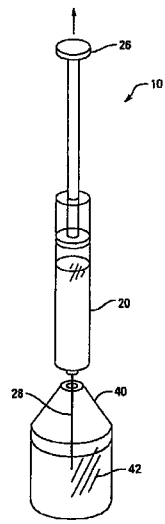

U.S. PATENT DOCUMENTS

| | | | |
|---|---|---|---|
| 5,529,577 A | 6/1996 | Hammerslag | |
| 5,532,311 A | 7/1996 | Sirvio et al. | |
| 5,571,181 A | 11/1996 | Li | |
| 5,585,007 A | 12/1996 | Antanavich et al. | |
| 5,591,205 A | 1/1997 | Fowler | |
| 5,601,602 A | 2/1997 | Fowler | |
| 5,624,669 A | 4/1997 | Leung et al. | |
| 5,674,394 A * | 10/1997 | Whitmore | 210/321.8 |
| 5,676,689 A | 10/1997 | Kensey et al. | |
| 5,716,375 A | 2/1998 | Fowler | |
| 5,741,223 A | 4/1998 | Janzen et al. | |
| 5,788,662 A | 8/1998 | Antanavich et al. | |
| 5,795,571 A | 8/1998 | Cederholm-Williams et al. | |
| 5,814,066 A | 9/1998 | Spotnitz | |
| 5,830,130 A | 11/1998 | Janzen et al. | |
| 5,843,124 A | 12/1998 | Hammerslag | |
| 5,916,236 A | 6/1999 | Muijs Van de Moer et al. | |
| 5,957,952 A | 9/1999 | Gershony et al. | |
| 6,007,563 A | 12/1999 | Nash et al. | |
| 6,033,427 A | 3/2000 | Lee | |
| 6,146,771 A | 11/2000 | Wirt et al. | |
| 6,197,289 B1 | 3/2001 | Wirt et al. | |
| 6,482,223 B1 * | 11/2002 | Nowakowski et al. | 606/213 |
| 6,521,265 B1 * | 2/2003 | Patterson | 424/646 |

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 33 is cancelled.

Claims 1, 2, 13, 21, 29, 34, 40, 46, 56 and 62 are determined to be patentable as amended.

Claims 3-12, 14-20, 22-28, 30-32, 35-39, 41-45, 47-55, 57-61 and 63-72, dependent on an amended claim, are determined to be patentable.

1. A system for closing a puncture wound in a patient comprising:
   a chamber that accommodates a volume of *whole* blood from the patient;
   a preloaded reversible anticoagulant in the chamber *in a quantity that provides anticoagulation for the volume of whole blood when it is free of exogenous anticoagulants*;
   a *predetermined amount of a* counteracting agent for *chemically* counteracting the *quantity of* reversible anticoagulant [that user causes to selectively interact with at least a portion of the volume of blood]; and
   an apparatus *comprising the chamber* to transfer the volume of blood from the patient to the chamber [and to transfer the portion of the volume of blood from the chamber to the puncture wound after the user causes the counteracting agent to selectively interact with the portion of the volume of blood] *to thereby combine the whole blood and the reversible anticoagulant in the chamber, to subsequently selectively interact the counteracting agent with the combination of whole blood and reversible anticoagulant to thereby form reversed blood in the chamber, and to subsequently transfer the reversed blood from the chamber to the patient, wherein the apparatus comprises the reversed whole blood*.

2. The system of claim 1 *wherein the apparatus is further* comprising:
   an activating material for activating the [portion of the volume of blood after the user causes the counteracting agent to selectively interact with the portion of the volume of] *reversed* blood.

13. The system of claim 1 wherein the apparatus utilizes a common conduit to transfer the volume of blood to the chamber and to transfer the [portion of the volume of] blood to the puncture wound.

21. The system of claim *1* wherein the reversible anticoagulant binds calcium ions.

29. The system of claim *1* further comprising anti-lytic agents selectively exposable to the volume of blood by a user.

34. A method for treating a wound in a patient comprising:
   withdrawing a volume of *whole* blood from the patient into a chamber *in an apparatus*, the blood being substantially free of anticoagulants;
   inhibiting clotting of the volume of *whole* blood with an anticoagulant preloaded in a chamber;
   storing the volume of blood in the chamber;
   applying a counteracting agent to *the* at least a portion of the volume of blood *in the apparatus* to counteract the action of the anticoagulant *and thereby forming reversed whole blood*; and applying the portion of the volume of blood *from the apparatus* to the wound.

40. The method of claim 39 wherein the activating material is non [bilogical] *biological* in origin.

46. A system for treating a wound in a patient comprising:
   a chamber that accommodates a volume of *whole* blood from the patient;
   a preloaded reversible anticoagulant in the chamber *in a quantity that provides anticoagulation for the volume of whole blood when it is free of exogenous anticoagulants*;
   *a predetermined amount of a counteracting agent for chemically counteracting the quantity of reversible anticoagulant;*
   an activating material that a user causes to selectively interact with at least a portion of the volume of blood; and
   an apparatus *comprising the chamber* to transfer the volume of blood from the patient to the chamber *to thereby combine the whole blood and the reversible anticoagulant in the chamber, to subsequently selectively interact the counteracting agent with the combination of whole blood and reversible anticoagulant to thereby form reversed blood in the chamber*, and to transfer the portion of the volume of blood from the chamber to the wound after the user causes the activating material to selectively interact with the portion of the volume of blood *to thereby form reversed and activated whole blood in the apparatus, wherein the activating material remains within the apparatus*.

56. The system of claim 46 wherein the reversible [antocoagulant] *anticoagulant* is selected from a group consisting of heparin, hirudin, pentasaccharide, low molecular weight heparin, and DANAPAROID™.

62. A method for treating a wound in a patient comprising:
   withdrawing [an] *a* volume of *whole* blood from the patient into a chamber, the blood being substantially free of anticoagulants;
   inhibiting clotting of the volume of blood with an anticoagulant preloaded in the chamber; storing the volume of blood in the chamber;
   *treating the blood with a counteracting agent to thereby form reversed blood in the chamber, and* exposing at least a portion of the volume of blood to an activating material *immobilized to a solid phase, wherein the activating material does not leave the solid phase and is not applied to the wound*; and
   applying the portion of the volume of blood to the wound.

* * * * *